United States Patent
Bíte et al.

[11] 4,028,348
[45] June 7, 1977

[54] 6-AMINO-5β,19-CYCLOANDROSTANE DERIVATIVES

[75] Inventors: Pál Bíte; Imre Moravcsik; Inge Scháfer; Gyula Horváth; Zsuzsanna Méhesfalvi née Vajna; János Borvendég; Ilona Hermann née Szente, all of Budapest, Hungary

[73] Assignee: Richter Gedeon Vegyeszeti Gyar RT, Budapest, Hungary

[22] Filed: Feb. 17, 1976

[21] Appl. No.: 658,863

[52] U.S. Cl. .................. 260/239.5; 260/239.55 R; 260/239.55 C; 260/397.3; 260/397.4; 260/397.5
[51] Int. Cl.² .................. C07J 41/00; C07J 43/00
[58] Field of Search .................. 260/239.5; /Machine Searched Steroids

[56] References Cited
UNITED STATES PATENTS
3,912,722  10/1975  Mukawa .................. 260/239.5

Primary Examiner—Elbert L. Roberts
Attorney, Agent, or Firm—Young & Thompson

[57] ABSTRACT

Novel 6-amino-5β,19-cycloandrostane derivatives of formula I and their pharmaceutically acceptable addition salts (I)

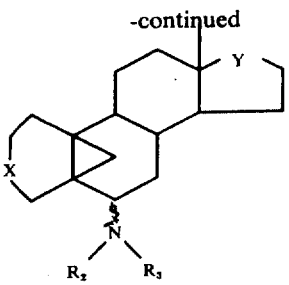

wherein
X denotes any of the groups of the formula =CH(OR), =CO or =C=N-OR₁,
Y denotes any of the groups of the formula =CO, =CH(OR₁), =C=N-OR₁, =C(OR₁)-C≡CH or

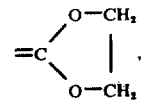

wherein
R denotes a hydrogen atom, a $C_{1-4}$ alkyl group or a $C_{2-5}$ acyl group, and
R₁ denotes a hydrogen atom, a straight-chained or branched $C_{1-5}$ alkyl group, a straight-chained or branched $C_{1-5}$ hydroxyalkyl group, a $C_{3-8}$ cycloalkyl group, an allyl group, or a benzyl group, and
R₃ has the same meaning as R₂ but if R₂ is a sec. or tert. alkyl group or an alicyclic group, then R₃ can only be a hydrogen atom; and if R₂ is a benzyl group then R₃ can only be a hydrogen atom or a primary alkyl group, further R₂ and R₃ may denote together with the adjacent nitrogen atom a piperidine, a morpholine, or an N-methylpiperazine group. These compounds have exhibited an aldosterone-antagonistic effect on rats.

1 Claim, No Drawings

6-AMINO-5β,19-CYCLOANDROSTANE DERIVATIVES

This invention relates to novel 6-amino-5β,19-cycloandrostane derivatives of the general formula I and to their acid addition salts.

In the formula I

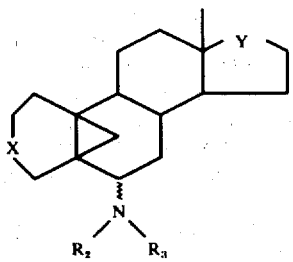
(I)

X denotes any of the groups of the formula =CH(OR), =CO or =C=N-OR$_1$,

Y denotes any of the groups of the formula =CO, =CH(OR$_1$), =C=N-OR$_1$, =C(OR$_1$)-C = CH or

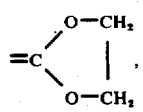

wherein

R denotes a hydrogen atom, a C$_{1-4}$ alkyl group of a C$_{2-5}$ acyl group, and R$_1$ denotes a hydrogen atom or a C$_{2-5}$ acyl group, R$_2$ denotes a hydrogen atom, or a C$_{1-5}$ aliphatic group with a straight or branched carbon chain carrying no substituent or substituted with a hydroxy, a C$_{1-4}$ alkoxy or an acyloxy group, or a C$_{3-8}$ alicyclic group, or an allyl group, or a C$_{7-10}$ aralkyl group carrying no substituent or substituted on the aromatic ring with a C$_{1-4}$ alkoxy group, R$_3$ has the same meaning as R$_2$ but if R$_2$ is a sec. or tert. alkyl group or an acyclic group, then R$_3$ can only be a hydrogen atom; and if R$_2$ is an aralkyl group then R$_3$ can only be a hydrogen atom or a primary alkyl group, further R$_2$ and R$_3$ may denote together with the nitrogen atom a pyrrolidine, a piperidine, a morhpoline, a piperazine, an N-alkyl piperazine, an N-oxyalkyl piperazine, an N-(alkoxy-alkyl)-piperazine, an N-(acyloxy-alkyl)-piperazine or an N-aralkyl piperazine group.

If R denotes a C$_{1-4}$ alkyl group, the latter may be preferably a methyl group. If R denotes a C$_{2-5}$ acyl group, this may be preferably an acetyl or propionyl group.

If R$_1$ denotes a C$_{2-5}$ acyl group, this may be preferably an acetyl or propionyl group.

If R$_2$ denotes a C$_{1-5}$ straight-chain alkyl group, this may be preferably a methyl, ethyl, n-propyl or n-butyl group. If R$_2$ denotes a branched-chain alkyl group, this may be preferably an isopropyl, isobutyl or tert. isobutyl group. If R$_2$ denotes an aliphatic group carrying a hydroxy group as substituent, this may be preferably a 2 hydroxyethyl or 3-hydroxypropyl group. If R$_2$ denotes an aliphatic group carrying an alkoxy substituent, this may be preferably a 2-methoxyethyl, 2-ethoxyethyl or 3-methoxypropyl group. If R$_2$ denotes an aliphatic group carrying an acyloxy substituent, this may be preferably a 2-acetoxyethyl, 3-acetoxypropyl, 2-trimethoxybenzoyl-ethyl or 3-trimethoxybenzoyl-propyl group. If R$_2$ denotes an alicyclic group, this may be preferably a cyclopropyl or a cyclohexyl group. If R$_2$ denotes an unsubstituted aralkyl group, this may be preferably a benzyl group. If R$_2$ denotes an aralkyl group carrying an alkoxy substituent, this may be preferably a p-methoxybenzyl group.

If R$_2$ and R$_3$ denote, together with the nitrogen atom, an N-alkyl piperazine group, this may be preferably an N-methyl piperazine group. If R$_2$ and R$_3$ denote, together with the nitrogen atom, an N-oxyalkyl piperazine group, this may be preferably an N-(2-hydroxyethyl)-piperazine or an N-(3-hydroxypropyl)-piperazine group. If R$_2$ and R$_3$ denote, together with the nitrogen atom, an N-(alkoxyalkyl)piperazine group, this may be preferably an N-(2-methoxyethyl)-piperazine, an N-(3-methoxypropyl)-piperazine or an N-(3-ethoxypropyl)-piperazine group. If R$_2$ and R$_3$ denote, together with the nitrogen atom, an N-(acyloxyalkyl)piperazine group, this may be preferably an N-(2-acetoxyethyl)-piperazine or an N-(3-trimethoxybenzoyl-propyl)piperazine group. If R$_2$ an R$_3$ denote, together with the nitrogen atom, an N-aralkyl piperazine group, this may be preferably an N-benzyl piperazine group.

It is known that many of the steroids occurring in nature or prepared in a semi-synthetic or synthetic way are of prominent significance in therapy. In recent years, e.g. of the semisynthetic steroids containing a nitrogen atom the pancuronium bromide has been found widespread application in chirurgical anaesthetizing due to its effect which exceeds that of d-tubocurarine and is more advantageous.

The invention aims at developing nitrogen-containing novel steroid derivatives possessing valuable pharmacological properties. The invention is based on the recognition that on reacting steroids of the general formula II

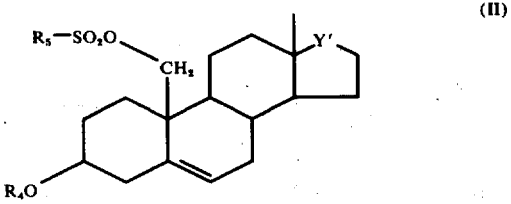
(II)

wherein

Y' denotes a carbonyl or an ethylene-ketal group,

R$_4$ denotes a C$_{1-4}$ alkyl group or a C$_{2-5}$ acyl group, and

R$_5$ denotes a C$_{1-4}$ alkyl, a phenyl or a tolyl group, with a secondary or primary amine of the general formula III

(III)

wherein R$_2$ and R$_3$ have the same meaning as above, compounds of the general formula I can be produced wherein R$_2$ and R$_3$ have the same meaning as above, X denotes a group of the formula =CH(OR), wherein R has the above-given meaning, and Y denotes a carbonyl or an ethyleneketal group.

Tadanier and Cole (Tetrahedron Letters 1964, 1345) reported on the conversion of 3β-methoxy-19-mesyloxy-Δ⁵-androsten-17-one, a compound belonging to the group of compounds of the general formula II, which conversion occurs in aqueous acetone on the effect of potassium acetate buffer. On hydrolysis, the reaction product is 3β-methoxy-6α-hydroxy-5β,19-cycloandrostan-17-one. Almost at the same time also Halpern et al. reported (Steroids 4, 1/1964/) that on boiling 3β-acetoxy-19-tosyloxy-Δ⁵-androsten-17-one in pyridine, 3β-acetoxy-5β,19-cycloandrost-6-en-17-one was obtained. According to the British Patent Specification No. 1,049,317, the compounds of the general formula II are converted in aqueous acetone, in the presence of a buffer containing potassium acetate, into 6α-hydroxy-5β,19-cycloandrostane derivatives. It was described by Tadanier (J. Org. Chem. 31, 3204 /1966/) that on boiling the above-mentioned 3β-methoxy-19-mesyloxy-Δ⁵-androsten-17-one in glacial acetic acid, in the presence of acetic anhydride, and hydrolyzing the product, 3β-methoxy-6β-(hydroxymethyl)-ester-5(10)-en-17-one is formed.

The above data indicate that though the reactions of compounds of the general formula II with a potassium acetate buffer in aqueous acetone, further with pyridine and with glacial acetic acid have been investigated, up to the present no data can be found concerning the reaction of compounds of the general formula II with secondary or primary amines.

The novel 6-amino-5β-19-cycloandrostane derivatives of the general formula I and their acid addition salts — in which formula X denotes any of the groups of the formula =CH(OR), =CO or =C=N-OR₁, Y denotes any of the groups of the formula =CO, =CH(OR₁), =C=N-OR₁, =C(OR₁)-C ≡ CH or

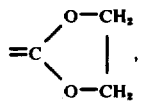

wherein

R denotes a hydrogen atom, a C₁₋₄ alkyl group or a C₂₋₅ acyl group, and R₁ denotes a hydrogen atom or a C₂₋₅ acyl group, R₂ denotes a hydrogen atom, or a C₁₋₅ aliphatic group with a straight or branched carbon chain carrying no substituent or substituted with a hydroxy, a C₁₋₄ alkoxy or an acyloxy group, or a C₃₋₈ alicyclic group, an allyl group, or a C₇₋₁₀ aralkyl group carrying no substituent or substituted on the aromatic ring with a C₁₋₄ alkoxy group, R₃ has the same meaning as R₂ but if R₂ is a sec. or tert. alkyl group or an alicyclic group, then R₃ can only be a hydrogen atom; and if R₂ is an aralkyl group then R₃ can only be a hydrogen atom or a primary alkyl group, further R₂ and R₃ may denote together with the nitrogen atom a pyrrolidine, a piperidine, a morpholine, a piperazine, an N-alkyl piperazine, an N-oxyalkyl piperazine, an N-(alkoxy-alkyl)-piperazine, an N-(acyloxy-alkyl)-piperazine or an N-aralkyl piperazine group — can be prepared in compliance with the process according to the invention by reacting a steroid of the general formula II — wherein Y' denotes a carbonyl or an ethylene-ketal group, R₄ denotes a C₁₋₄ alkyl or a C₂₋₅ acyl group, and R₅ denotes a C₁₋₄ alkyl, a phenyl or a tolyl group — with a secondary or primary amine of the general formula III, wherein R₂ and R₃ have the same meaning as above, and, if desired, converting the obtained compound of the general formula I, wherein R₂ and R₃ have the same meaning as above, X denotes a group of the formula =CH(OR), wherein R has the above-given meaning and Y denotes a carbonyl or an ethylene-ketal group, by hydrolysis and/or by oxidation and/or by oxime formation and/or by ethynylation and/or by acylation and/or by reduction into another compound of the general formula I, and, if desired, the obtained compound of the general formula I is transformed by reacting with a pharmaceutically acceptable acid into an acid addition salt.

Pharmacological investigations on the novel compounds of the general formula I were carried out with their therapeutically acceptable water-soluble salts, in general with their hydrochlorides. A group of these novel compounds exhibited on rats an aldosterone-antagonistic effect. The efficient dose levels amounted to from 2 to 10 mg./kg. in the case of subcutaneous administration. Their effect was nearly identical with the diuretic activity of spironolactone β(7α-acetylthio-17β-hydroxy-3-oxandrost-4-en-17β-yl) propionic acid γ-lactone, applied at present in therapy. This effect manifested itself in a significant rise of the Na/K quotient of urine. The data of acute toxicity were favourable. In castrated male mice (1.5 mg./2 weeks) and in infantile male rats (9 mg./2 weeks) no androgenic, anabolic, antiandrogenic, antigonadotropic or thymolytic effects were observed. In infantile female mice no uterotropic or antiestrogenic effects were observed.

In compliance with a preferable method of implementation of the process for producing compounds according to the invention 1 mole of a compound of the general formula II is dissolved in 2 to 20 moles of an amine of the general formula III, or identical amounts of compounds I and III are dissolved or suspended in dimethyl formamide or dimethyl acetamide or a C₂₋₇ aliphatic alcohol, and the reaction mixture is heated at atmospheric pressure or in a sealed tube to a temperature between 70° and 180° C, then kept at this temperature for a period of 1 to 10 hours. The excess of the reagent of the general formula III is removed by vacuum distillation and/or by dissolving the reaction mixture in an organic solent immiscible with water and subsequent washing with water. The distillation residue of the anhydrous organic phase is dissolved in anhydrous ethanol or ether, and the reaction product of basic character is precipitated as salt with the ethanolic or ethereal solution of an appropriate acid, e.g. hydrochloric, maleic, perchloric etc. acid. The desired compound of the general formula I, wherein R₂ and R₃ have the same meaning as above, X denotes a group of the formula =CH(OR), wherein R has the above-given meaning, and Y denotes a carbonyl or an ethylene-ketal group, is obtained from the formed mixture by crystallization and/or, after liberation of the base, by column chromatography. If desired, the thus-obtained product can be converted by hydrolysis, oxidation, oxime formation, ethynylation, acylation, reduction or a combination of these methods into an other compound of the general formula I in a known way.

The starting compounds of the general formula II of the process according to the invention are compounds already known in literature. The physical constants of 3β-acetoxy-19-tosyloxy-Δ⁵-androsten-17-one were described in 1963 (Chem. and Ind. 1963, 116), and its preparation was published in 1966 (J. Org. Chem. 31, 693 /1966/) by Halpern et al. The preparation of 3β-methoxy-19-hydroxy-Δ⁵-androsten-17-one was described in 1963 by Tadanier (J. Org. Chem. 28, 1744 /1963/). Compounds of the general formula II — with the exception of the 17-ethylene-ketal compounds — are described in the British Patent Specification 1,049,317 as starting compounds. The 17-ethylene-dioxy derivatives can be prepared from the latter compounds by known methods.

The novel compounds of general formula I and their method of preparation are further illustrated by the following non-limiting Examples.

EXAMPLE 1

3β-Acetoxy-6ξ-dimethylamino-17-oxo-5β,19-cycloandrostane hydrogen perchlorate 5.00 g. (0.01 moles) of 3β-acetoxy-17-oxo-19-tosyloxy-Δ⁵-androstene and 20 ml. of anhydrous N,N-dimethyl acetamide containing 22% by weight of dimethyl amine are heated in a sealed tube to 110° C and kept at this temperature for 7 hours. On cooling, the contents of the sealed tube are poured into 400 ml. of ice-water and stirred for 15 minutes. The formed precipitate is filtered, washed with water, and then dissolved in 150 ml. of benzene. The benzene solution is washed with water, dried and evaporated under vacuum. On dissolving the residue in 20 ml. of anhydrous ethanol, the solution is neutralized with ethanol containing perchloric acid. On allowing the solution to stand for 2 hours at a temperature between 0° and −5° C, it is filtered, the crystalline substance is washed with anhydrous ethanol and dried under vacuum at 60° C. The product weighs 1.70 g.; m.p. 200°–203° C; after recrystallization from methanol, m.p. 208°–209° C.

EXAMPLE 2

3β-Acetoxy-6ξ-diethylamino-17-oxo-5β,19-cycloandrostane hydrogen perchlorate 10 g. (0.02 moles) 3β-acetoxy-17-oxo-19-tosyloxy-Δ⁵-androstene and 25 ml. (0.24 moles) of freshly distilled diethyl amine are heated in a sealed tube to 130° C and kept at this temperature for 5 hours. On cooling, the reaction mixture is evaporated under vacuum. The residue is rubbed with 50 ml. of benzene. The formed precipitate is filtered and washed with benzene. The combined filtrates are washed with water, dried and evaporated under vacuum. The obtained viscous oil is dissolved in 20 ml. of anhydrous ethanol and neutralized with perchloric acid containing ethanol. On allowing the solution to stand for a few hours the formed crystals are filtered, washed with anhydrous ethanol and dried under vacuum at 60° C. The product weighs 3.20 g. (32%); m.p. 181°–183° C; after recrystallization from methanol, m.p. 184°–185° C.

EXAMPLE 3

3β-Acetoxy-6ξ-piperidino-17-oxo-5β,19-cycloandrostane hydrogen perchlorate

Method (a)

20 g. (0.04 moles) of 3β-acetoxy-17-oxo-19-tosyloxy-Δ⁵-androstene are dissolved hot in 20 ml. (0.20 moles) of freshly distilled piperidine, then the reaction mixture is refluxed for 5 hours on a 150° C oil bath. On cooling, excess piperidine is distilled off under vacuum and the evaporation residue is rubbed with 50 ml. of benzene. The sedimented piperidine salt is filtered and washed with 2 × 10 ml. of benzene. Traces of piperidine are removed from the filtrate by shaking it with water. The benzene phase is dried with sodium sulphate, then evaporated under vacuum. The obtained viscous oil is dissolved in 20 ml. of anhydrous ethanol, and the solution neutralized with perchloric acid containing ethanol. On allowing the solution to stand for 2 hours, the formed crystals are filtered and washed with some anhydrous ethanol. On drying the product under vacuum at 60° C, it weighs 10.5 g. (51%); m.p. 206°–210° C; after recrystallization from methanol, m.p. 214°–216° C.

M.p. of the maleinate: 202°–205° C (from ethanol).

Method (b)

20 g. (0.04 moles) of 3β-acetoxy-17-oxo-19-tosyloxy-Δ⁵-androstene are dissolved in 200 ml. of anhydrous dimethyl formamide, and 12 ml. (0.12 moles) of freshly distilled piperidine added. After heating the reaction mixture to 100° C, it is kept at this temperature for 10 hours, then evaporated to dryness under vacuum. The further procedure is the same as described with method (a). The product is identical with that of method (a); the yield amount to 41%.

Method (c)

20 g. (0.04 moles) of 3β-acetoxy-17-oxo-19-tosyloxy-Δ⁵-androstene are dissolved in 80 ml. of anhydrous isopropanol, then 12 ml. (0.12 moles) of freshly distilled piperidine are added. On refluxing the reaction mixture for 3 hours, it is cooled and evaporated to dryness under vacuum. The further procedure is the same as described with method (a). The product is identical with that of method (a); the yield is 40%.

EXAMPLE 4

3β-Acetoxy-6ξ-(N-methylpiperazino)-17-oxo-5β,19-cycloandrostane hydrochloride

Starting from 20 g. (0.04 moles) of 3β-acetoxy-17-oxo-19-tosyloxy-Δ⁵-androstene and 20 ml. of N-methylpiperazine, one proceeds exactly in the same way as specified in method (a) of Example 3 but the product is isolated as hydrochloride. Yield: 9.00 g. (48%); m.p. 213°–215° C.

EXAMPLE 5

3β-Acetoxy-6ξ-morpholino-17-oxo-5β,19-cycloandrostane hydrogen perchlorate

Starting from 20 g. (0.047 moles) of 3β-acetoxy-17-oxo-19-mesyloxy-Δ⁵-androstene and 20 ml. (0.23 moles) of freshly distilled morpholine, and proceeding in the way as specified in method (a) of Example 3, 11.80 g. (49%) of product are obtained; m.p. 202°–204° C; after recrystallization from a mixture of methanol and water, m.p. 207°–208° C; m.p. of the hydrochloride: 214°–217° C (from ethanol).

EXAMPLE 6

3β-Acetoxy-6ξ-tert.butylamino-17-oxo-5β,19-cycloandrostane hydrochloride 10 g. (0.02 moles) of 3β-acetoxy-17-oxo-19-tosyloxy-Δ⁵-androstene and 22 ml. (0.21 moles) of freshly distilled tert.butyl amine are heated in a sealed tube to 150° C and kept at this temperature for 5 hours. Then the reaction mixture is processed in the way as specified in Example 2, with the difference, however, that the residue obtained on evaporating the benzene solution to dryness is dissolved in anhydrous ether, and the hydrochloride is prepared by means of anhydrous ether saturated with dry hydrochloric acid gas. Yield: 3.9 g. (45%); m.p. 207°–208° C; after recrystallization from anhydrous ethanol, m.p. 208°–210° C.

EXAMPLE 7

3β-Acetomy-6ξ-cyclohexylamino-17-oxo-5β,19-cycloandrostane hydrochloride 10 g. (0.02 moles) of 3β-acetoxy-17-oxo-19-tosyloxy-Δ$^5$-androstene are dissolved in 20 ml. (0.18 moles) of freshly distilled hot cyclohexyl amine then the reaction mixture is refluxed for 5 hours on a 160° C oil bath. On cooling, the excess of cyclohexyl amine is distilled off under vacuum, and the evaporaton residue is rubbed with 50 ml. of benzene. The formed precipitate is filtered and washed with 2 × 10 ml. of benzene. Traces of cyclohexyl amine are removed from the combined benzene phases by shaking with water, then the benzene is dried and evaporated under vacuum. The obtained thick, viscous oil is dissolved in 30 ml. of ether and neutralized by adding ether saturated with dry hydrochloric acid gas. After allowing the mixture to stand for two hours the formed precipitate is filtered, washed with ether and dried at 60° C under vacuum, affording 8.50 g. of the crude product.

On dissolving the crude product in 200 ml. of water, the aqueous solution is shaken with 33 × 30 ml. of benzene, the aqueous phase made alkaline with a 10% solution of sodium hydroxide and extracted with 3 × 50 ml. of benzene. The benzene solution is washed with water, dried, and evaporated under vacuum. The residue is dissolved in anhydrous ethanol and neutralized with ethanol saturated with dry hydrochloric acid gas. The neutral solution is evaporated and the residue rubbed with acetone. The formed crystals are filtered, washed with acetone and dried at 60° C under vacuum, affording 5.30 g. of the product; m.p. 219°–221° C; after recrystallization from a mixture of acetone and hexane, m.p. 223°–225° C.

EXAMPLE 8

3β-Acetoxy-6β-benzylamino-17-ethylenedioxy-5β,19-cycloandrostane hydrochloride 1.00 g. (184 millimoles) of 3β-acetoxy-17-ethylenedioxy-19-tosyloxy-Δ$^5$-androstene is dissolved in 3.00 ml. of N,N-dimethyl acetamide and 1.00 ml. (9.10 millimoles) of freshly distilled benzyl amine by heating, then the reaction mixture is heated to 110° C and kept at this temperature for 3.5 hours. After cooling the homogeneous solution is poured slowly, under continuous stirring, to 150 ml. ice-water, then the precipitate formed after 15 minutes of stirring is filtered, dissolved in 60 ml. of benzene and washed with water. On drying, the solution is evaporated under vacuum, the residue dissolved in 15 ml. of anhydrous ethanol, neutralized with ethanol saturated with dry hydrochloric acid gas, and evaporated to dryness under vacuum at a temperature below 50° C. The obtained viscous oil turns crystalline on rubbing with some acetone. The crystals are filtered, washed with acetone and dried under vacuum at 60° C, affording 0.45 g. (44%) of the product; m.p. 234°–236° C; after recrystallization from methanol, m.p. 239°–241° C.

EXAMPLE 9

3β-Acetoxy-6ξ-cyclohexylamino-17-ethylenedioxy-5β,19-cycloandrostane hydrochloride 1.00 g. (184 millimoles) of 3β-acetoxy-17-ethylenedioxy-19-tosyloxy-Δ$^5$-androstene are dissolved hot in 3.00 ml. of N,N-dimethyl acetamide and 1.00 ml. (8.74 millimoles) of freshly distilled cyclohexyl amine. The reaction mixture is heated to 110° C and kept at this temperature for 2.5 hours.

In the following one proceeds in the same way as specified in Example 8. Yield: 0.50 g. (50 %); m.p. 218°–220° C; after recrystallization from a mixture of acetone and hexane, m.p. 224°–227° C.

EXAMPLE 10

3β-Acetoxy-17-ethylenedioxy-6ξ-cyclopropylamino-5β,19-cycloandrostane hydrochloride.

10 g. (18,4 mmoles) of 3β-acetoxy-17-ethylenedioxy-19-tosyloxy-Δ$^5$-androstene and 6.4 ml. (92.0 mmoles) of freshly distilled cyclopropylamine are dissolved under warming in 50 ml. of N,N-dimethyl acetamide. The obtained solution is warmed to 95° C and kept at this temperature for 5 hours. After cooling the solution is allowed to slowly flow under constant stirring to 1 liter of ice-water. The separated precipitate is quickly filtered, washed with water and dissolved from the filter with 150 ml. of benzene. The benzene solution is washed with water, dried with sodium sulphate and evaporated to dryness under vacuum. The distillation residue is dissolved in 30 ml. of ether and neutralized with ether saturated with dry hydrochloric acid gas. The separated precipitate is filtered, washed with ether and thereafter with petroleum ether and dried under infra-red lamp. The thus-obtained crude product weighing 4.80 g. is suspended in benzene, filtered, washed with a 1:1 mixture of benzene and petroleum ether, and dried at 60° C under vacuum. The product weights 3.80 g. (44%); m.p. 212°–214° C. After recrystallization from isopropanol, m.p. 218°–220° C.

EXAMPLE 11

3β-Acetoxy-17-oxo-6ξ-allylamino-5β,19-cycloandrostane hydrochloride 5.44 g. (0.01 moles) of 3β-acetoxy-17-ethylenedioxy-19-tosyloxy-Δ$^5$-androstene and 3 ml. (0.04 moles) of freshly distilled allyl amine are dissolved under warming in 20 ml. of anhydrous N,N-dimethyl acetamide. The temperature of the solution is raised to 110° C and kept at this value for 2.5 hours. Thereafter the reaction mixture is cooled to room temperature and is dropped into 200 ml. of ice-water under vigorous stirring. The separated precipitate is quickly filtered and then dissolved with benzene from the filter. The benzene solution is washed with water, dried with sodium sulphate and evaporated under vacuum. The residue is dissolved in anhydrous ethanol. The pH of the solution is set to a value of 4 with ethanol saturated with dry hydrochloric acid gas, and the solution is allowed to stand for a night at room temperature. Thereafter it is evaporated to dryness at 60° C under vacuum. The residue is a viscous oil which solidifies when rubbing with ether. The crude product is filtered, washed with ether and dried under infra-red lamp. Yield: 2.00 g. (47.5%); m.p. 208°–211° C. After recrystallization from isopropanol, m.p. 215°–216° C.

EXAMPLE 12

3β-Methoxy-17-oxo-6ξ-piperidino-5β,19-cycloandrostane hydrochloride 5 g. (0.013 moles) of 3β-methoxy-17-oxo-19-mesyloxy-Δ⁵-androstene are dissolved under warming in 15 ml. of anhydrous N,N-dimethyl acetamide and 5.2 ml. (0.052 moles) of freshly distilled piperidine. The reaction mixture is warmed to 110° C and kept at this temperature for 4 hours. After cooling the solution is allowed to slowly flow while constant stirring to 500 ml. of ice-water. After stirring for 10 minutes the separated precipitate is filtered and dissolved in 100 ml. of benzene. The benzene solution is washed with water, dried with sodium sulphate and evaporated under vacuum. The residue is dissolved in 20 ml. of anhydrous ethanol and neutralized with ethanol saturated with dry hydrochloric acid gas. The neutral solution is evaporated to dryness under vacuum, and the residue is rubbed with benzene. The solidified product is washed with some benzene and thereafter with 1:1 mixture of acetone and petroleum ether, then dried in a vacuum exsiccator at 60° C. The product weighs 2.70 g. (51%); m.p. 217°–220° C. After recrystallization from isopropanol, m.p. 222°–224° C.

EXAMPLE 13

3β-Acetoxy-6ξ-piperidino-5β,19-cycloandrostane-17-oxime hydrochloride 2 g. (0.004 moles) of 3β-acetoxy-6ξ-piperidino-17-oxo-5β,19-cycloandrostane hydrogen perchlorate are vigorously stirred with 5 ml. of a 20% aqueous solution of sodium hydroxide and 30 ml. of benzene at room temperature for 15 minutes. On separating the two phases in a separating funnel, the aqueous phase is extracted with 2 × 10 ml. of benzene. The combined benzene phases are washed with water, dried and evaporated under vacuum, affording 1.40 g. of a viscous oil. This oil is dissolved in 30 ml. of anhydrous ethanol. After addition of 0.48 g. (0.007 moles) of hydroxylamine hydrochloride and 0.92 g. (0.01 moles) of anhydrous sodium acetate, the reaction mixture is refluxed for 4 hours, then filtered. The filtrate is evaporated to dryness under vacuum, and the residue is dissolved in 60 ml. of water. The solution is made alkaline with a 10% aqueous solution of sodium hydroxide and extracted with 3 × 20 ml. of chloroform. The chloroform phase is washed with water, dried and evaporated to dryness under vacuum. The syrup obtained in this way is dissolved in 10 ml. of anhydrous ethanol and neutralized with ethanol saturated with dry hydrochloric acid gas. The neutral solution is evaporated to one third of its initial volume and then allowed to stand overnight in a refrigerator. The formed crystals are filtered, washed with ethanol and dried under vacuum at 60° C, affording 1.45 g. (78%) of the product; m.p. 224°–226° C; after recrystallization from anhydrous ethanol, m.p. 228°–230° C.

EXAMPLE 14

3β-Hydroxy-6ξ-dimethylamino-17-oxo-5β,19-cycloandrostane 10 g. (0.021 moles) of 3β-acetoxy-6ξ-dimethylamino-17-oxo-5β,19-cycloandrostane hydrogen perchlorate are dissolved in 340 ml. of hot methanol, and a solution of 10 g. (0.073 moles) of anhydrous potassium carbonate in 30 ml. of water is added. After refluxing the reaction mixture for 1.5 hours it is cooled, the formed salts are filtered off, and the filtrate is evaporated to 30 ml. under vacuum. The evaporation residue is extracted with ethyl acetate, the ethyl acetate solution is washed with water, dried with sodium sulphate and evaporated under vacuum until crystallization begins. On allowing the mixture to stand for a few hours, the formed product is filtered, washed with ethyl acetate and dried under vacuum at 60° C, affording 5.70 g. (82%) of the product; m.p. 118°–122° C; after recrystallization from a mixture of acetone and water, m.p. 123°–125° C.

EXAMPLE 15

3β-Hydroxy-6ξ-diethylamino-17-oxo-5β,19-cycloandrostane

On starting from 10 g. (0.020 moles) of 3β-acetoxy-6ξ-diethylamino-17-oxo-5β,19-cycloandrostane hydrogen perchlorate, on proceeds exactly as specified in Example 14, obtaining 5.90 g. (82%) of the product; m.p. 124°–125° C; after recrystallization from ethyl acetate, m.p. 128°–130° C.

EXAMPLE 16

3β-Hydroxy-6ξ-piperidino-17-oxo-5β,19-cycloandrostane 20 g. (0.038 moles) of 3β-acetoxy-6ξ-piperidino-17-oxo-5β,19-cycloandrostane hydrogen perchlorate are dissolved in 2000 ml. of methanol under heating, and the solution of 16 g. of anhydrous potassium carbonate in 30 ml. of water is added. The reaction mixture is refluxed for 1.5 hours, then cooled and filtered. The substance retained on the filter is washed with methanol and the combined filtrates are evaporated under vacuum until crystallization begins. On allowing the solution to stand for a few hours, the formed crystals are filtered, washed with water and dried under vacuum at 60° C, affording 13.0 g. (91%) of the product; m.p. 175°–178° C; after recrystallization from acetone, m.p. 178°–181° C.

EXAMPLE 17

3β-Hydroxy-6ξ-(N-methylpiperazino)-17-oxo-5β,19-cycloandrostane 10 g. (0.021 moles) of 3β-acetoxy-6ξ-(N-methylpiperazino)-17-oxo-5β,19-cycloandrostene hydrochloride are dissolved in 1000 ml. of methanol. The solution is treated at room temperature with a solution of 10 g. of anhydrous potassium carbonate in 20 ml. of water, then the reaction mixture is heated to boiling and refluxed for an hour. Subsequently, 80 ml. of water are added to the solution which is then evaporated under vacuum to a volume of 100 ml. The residue is extracted with 3 × 30 ml. of chloroform. The chloroform phase is washed with water, dried and evaporated under vacuum. The obtained thick oil crystallizes on rubbing. The crystals are filtered and washed with some cold acetone, affording 7.5 g. (89%) of the product; m.p. 182°–185° C.

M.p. of the hydrochloride: 208°–210° C.

EXAMPLE 18

3β-Hydroxy-6ξ-morpholino-17-oxo-5β,19-cycloandrostane hydrochloride

Starting from 20 g. (0.038 moles) of 3β-acetoxy-6ξ-morpholino-17-oxo-5β,19-cycloandrostane hydrogen perchlorate, one proceeds in the same way as specified in Example 8, with the difference, however, that the solution of the crude product in anhydrous ethanol is processed with ethanol, containing hydrochloric acid, to obtain the hydrochloride. On recrystallization from ethanol the product weighs 12.6 g. (87%); m.p. 198°–200° C.

EXAMPLE 19

3β-Hydroxy-6ξ-tert.butylamino-17-oxo-5β,19-cycloandrostane

Starting from 20 g. (0.046 moles) of 3β-acetoxy-6ξ-tert.butylamino-17-oxo-5β,19-cycloandrostane hydrochloride, one proceeds in the same way as specified in Example 16. Yield: 14.0 g. (85%); m.p. 197°–200° C; after recrystallization from a mixture of methanol and water, m.p. 204°–207° C.

EXAMPLE 20

3β-Hydroxy-6ξ-cyclohexylamino-17-ethylenedioxy-5β,19-cycloandrostane 1.00 g. (1.84 millimoles) of 3β-acetoxy-17-ethylenedioxy-19-tosyloxy-Δ$^5$-androstene is dissolved hot in 3.00 ml. (26.2 millimoles) of freshly distilled cyclohexyl amine. The reaction mixture is heated to 150° C and kept at this temperature for 5 hours. After cooling excess cyclohexylamine is distilled off under vacuum, and the residue is dissolved in a 1:1 mixture of benzene and water. Traces of cyclohexylamine are removed by shaking with water. The benzene solution is dried and evaporated under vacuum, affording a viscous oil which is dissolved in ether and neutralized by ether saturated with dry hydrochloric acid gas. The formed precipitate is filtered, washed with acetone and dried. The crude product weighs 0.58 g.

The solution of the crude product in 50 ml. of methanol is treated with a solution of 0.4 g. of anhydrous potassium carbonate in 2 ml. of water and the mixture refluxed for an hour. After cooling 10 ml. of water are added and the solution is evaporated under vacuum to one fourth of its initial volume. The residue is extracted with 3 × 10 ml. of ethyl acetate. The ethyl acetate phases are combined, washed with water, dried, and evaporated under vacuum, affording 0.38 g. of the product; m.p. 168°–172° C.

EXAMPLE 21

3β,17β-Dihydroxy-6ξ-piperidino-5β,19-cycloandrostane

To a solution of 3 g. (0.008 moles) of 3β-hydroxy-6ξ-piperidino-17-oxo-5β,19-cycloandrostane in 150 ml. of methanol, under continuous cooling and vigorous stirring, 1.5 g. (0.04 moles) of solid sodium borohydride are added at 10° to 15° C in small portions in 20 minutes. The reaction mixture is stirred for a further hour, and then water is added until a precipitate is formed. After filtering this precipitate, it is washed with water and dried under vacuum at 60° C over phosphorus pentoxide. The obtained amorphous substance is dissolved in hot acetone, then water is added to the solution until it turns turbid. After allowing the system to stand for a few hours, the crystalline product is filtered and dried under vacuum at 60° C, affording 2.0 g. (66%) of the product; m.p. 172°–174° C; on recrystallization from a mixture of acetone and water, m.p. 176°–178° C.

M.p. of the hydrochloride recrystallized from ethanol: 209°–211° C.

EXAMPLE 22

3β-Hydroxy-6ξ-piperidino-5β,19-cycloandrostane-17-oxime 20 g. (0.054 moles) of 3β-hydroxy-6ξ-piperidino-17-oxo-5β,19-cycloandrostane, 8 g. (0.11 moles) of hydroxylamine hydrochloride and 9 g. (0.11 moles) of anhydrous sodium acetate are mixed up in 460 ml. of anhydrous ethanol. The reaction mixture is heated to boiling, then refluxed for 2.5 hours. After cooling, the formed salts are filtered off, and the filtrate is evaporated to dryness. The residue is dissolved in 200 ml. of water, the solution is made alkaline with a 20% solution of sodium hydroxide and immediately extracted with 3 × 50 ml. of chloroform. The chloroform phase is washed with water, dried with sodium sulphate and evaporated under vacuum. On rubbing the residual thick syrup with acetone, the product crystallizes. Yield: 19.2 g. (92%); m.p. 202°–204° C; after recrystallization from a mixture of ethanol and water, m.p. 206°–208° C.

EXAMPLE 23

3β-Hydroxy-6ξ-piperidino-17α-ethynyl,17β-hydroxy-5β,19-cycloandrostane 11 g. (0.10 moles) of potassium tert.butylate are weighed into a 4-tube, round-bottomed 500 ml. flask equipped with stirrer, thermometer and pipes for gas inlet and outlet, under allowing dry nitrogen gas to pass through the system. The weighed substance is then suspended in 200 ml. of anhydrous tetrahydrofurane under stirring. The rinsing with nitrogen gas is finished and then dry refined acetylene gas is allowed to pass through the reaction mixture at a slow flow rate for 40 minutes under continuous stirring. Then the solution of 10 g. (0.027 moles) of 3β-hydroxy-6ξ-piperidino-17-oxo-5β,19-cycloandrostane in 100 ml. of anhydrous tetrahydrofurane is dropwise added to the reaction mixture in 40 minutes, under continuous passage of acetylene gas, keeping the temperature of the reaction mixture meanwhile at between 18° and 22° C. When the dropwise addition is terminated, the introduction of acetylene gas is continued for further 2 hours, keeping the temperature at between 18° and 22° C, then the apparatus is rinsed with nitrogen gas, and the orange-coloured jelly-like reaction mixture is poured, under stirring, onto the mixture of 100 ml. of saturated ammonium chloride solution and ice. On allowing the reaction mixture to stand for half an hour, the two phases are separated in a separating funnel, and the aqueous phase is extracted with 3 × 20 ml. of benzene. The organic phase is washed with a saturated aqueous solution of sodium chloride, dried with sodium sulphate and evaporated to dryness under vacuum. The residue is transferred into a filter, washed with some cold benzene and dried under vacuum at 60° C, affording 8.70 g. (81%) of the product; m.p. 205°–207° C; after recrystallization from acetone, m.p. 208°–211° C.

EXAMPLE 24

3,17-Dioxo-6ξ-dimethylamino-5β,19-cycloandrostane 5 g. (0.015 moles) of 3β-hydroxy-6ξ-dimethylamino-17-oxo-5β,19-cycloandrostane, 150 ml. of anhydrous toluene and 29 ml. (0.28 moles) of distilled cyclohexanone are weighed into a round-bottomed 500 ml. flask equipped with a distilling attachment. Under atmospheric pressure 30 ml. of distillate are distilled off, then while continuing the distillation the solution of 1.5 g. (0.007 moles) of aluminium isopropylate in 15 ml. of anhydrous toluene is dropwise added to the reaction mixture in an hour. During the addition about 60 ml. of distillate are distilled off; subsequently another 30 ml. are distilled off. The residual reaction mixture is shaken with 2 × 10 ml. of a saturated aqueous solution of potassium sodium tartrate, then subjected to steam distillation. The residue is extracted with 3 × 20 ml. of ethyl acetate. The ethyl acetate phase is washed with water, dried and evaporated under vacuum to a small volume. On cooling the product crystallizes. After filtration and drying at 60° C under vacuum, 3.90 g. (78%) of product are obtained; m.p. 146°–150° C; after recrystallization from ethanol, m.p. 149°–152° C.

EXAMPLE 25

3,17-Dioxo-6ξ-diethylamino-5β,19-cycloandrostane hydrochloride 10 g. (0.028 moles) of 3β-hydroxy-6ξ-diethylamino-17-oxo-5β, 19-cycloandrostane, 270 ml. of anhydrous toluene and 58 ml. (0.56 moles) of distilled cyclohexanone are weighed into a round-bottomed 750 ml. flask equipped with a distilling attachment. In order to remove water from the reaction mixture, 30 ml. of distillate are distilled off under atmospheric pressure. On continuing the slow distillation, a solution of 5.8 g. (0.028 moles) of aluminium isopropylate in 40 ml. of anhydrous toluene is dropwise added to the reaction mixture in 1.5 hour, and meanwhile 100 ml. of distillate are distilled off. On distilling off further 50 ml. of distillate, the residue is cooled to room temperature, shaken with 2 × 20 ml. of a saturated aqueous solution of potassium sodium tartrate, then subjected to steam distillation, and the residue is extracted with 2 × 30 ml. of chloroform. The chloroform phase is washed with water, dried and evaporated to dryness under vacuum. On dissolving the obtained viscous oil in 20 ml. of anhydrous ethanol, the solution is neutralized with ethanol saturated with dry hydrochloric acid gas. The solution evaporated to one third of its initial volume is allowed to stand overnight in a refrigerator. The precipitated crystals are filtered, washed with ethanol and dried under vacuum at 60° C, affording 8.0 g. (80%) of the product; m.p. 205°–207° C; after recrystallization from a mixture of acetone and hexane, m.p. 212°–214° C.

EXAMPLE 26

3,17-Dioxo-6ξ-piperidino-5β, 19-cycloandrostane

Method (a): Oppenauer Oxidation 20.00 g. (0.05 moles) of 3β-hydroxy-6ξ-piperidino-17-oxo-5β, 19-cycloandrostane, 580 ml. of anhydrous toluene and 106 ml. of distilled cyclohexanone are weighed into a round-bottomed 1000 ml. flask equipped with a distilling attachment, and 60 ml. of distillate are distilled off the system at atmospheric pressure. Then, slowly continuing the distillation, a solution of 11.00 g. (0.054 moles) of aluminum isopropylate in 80 ml. of anhydrous toluene is dropwise added to the reaction mixture in an hour, meanwhile distilling off about 150 ml. of distillate. On continuing the distillation another 150 ml. of distillate are distilled off, the residue is cooled to room temperature, shaken with 2 × 20 ml. of a saturated aqueous solution of potassium sodium tartrate, and then subjected to steam distillation. The residue of the steam distillation is dissolved in 100 ml. of chloroform and repeatedly shaken with water. The chloroform phase is dried with sodium sulphate and evaporated under vacuum. A thick viscous oil is obtained which is dissolved hot in ether, and the ethereal solution is allowed to stand overnight whereafter 14.40 g. (72%) of crystallized product are obtained; m.p. 127°–129° C; after recrystallization from ether, m.p. 130°–132° C.

The hydrochloride recrystallized from a mixture of acetone and hexane melts at 253°–255° C.

Method (b): Jones Oxidation 2.0 g. (0.005 moles) of 3β-hydroxy-6ξ-piperidino-17-oxo-5β,19-cycloandrostane are dissolved in 40 ml. of anhydrous acetone, then 3.8 ml. of 8 N chromic acid are added dropwise to the reaction mixture in 30 minutes, under vigorous stirring, at a temperature between 10 and 15° C. Stirring is continued for further 2 hours at a temperature between 10° and 15° C, then excess chromic acid is decomposed by 3 ml. of isopropanol, and 40 ml. water are added to the reaction mixture. After stirring for 10 minutes, 4 g. of tartaric acid are added to the solution which is subsequently made alkaline with a 10% solution of sodium hydroxide, and shaken with 3 × 50 ml. of benzene. The benzene phase is washed with a saturated aqueous solution of sodium chloride, dried with sodium sulphate and evaporated under vacuum. The residue is dissolved in hot ether. On allowing the solution to stand, the product crystallizes. After filtration it is washed with cold ether and dried under vacuum at 60° C, affording a product identical with the substance obtained by the Oppenauer oxidation according to Method (a).

EXAMPLE 27

3,17-Dioxo-6ξ-(N-methylpiperazino)-5β,19-cycloandrostane

Starting from 20.0 g. (0.052 moles) of 3β-hydroxy-6ξ-(N-methylpiperazino)-17-oxo-5β, 19-cycloandrostane, and proceeding by the Oppenauer oxidation according to Example 26a, 14.40 g. (72%) of the free base are obtained; m.p. 202°–205° C.

After recrystallization from ethanol as hydrochloride, m.p. 236°–238° C.

EXAMPLE 28

3,17-Dioxo-6ξ-morpholino-5β,19-cycloandrostane

Starting from 20.0 g. (0.054 moles) of 3β-hydroxy-6ξ-morpholino-5β,19-cycloandrostane, and proceeding by the Oppenauer oxidation according to Example 26a, 13.60 g. (68%) of 3,17-dioxo-6ξ-morpholino-5β, 19-cycloandrostane are obtained; m.p. 138°–140° C (from ethanol).

The hydrochloride recrystallized from a mixture of acetone and hexane melts at 225°–228° C.

EXAMPLE 29

3,17-Dioxo-6ξ-tert.butylamino-5β,19-cycloandrostane

Starting from 5 g. (0.014 moles) of 3β-hydroxy-6ξ-tert.butylamino-17-oxo-5β,19-cycloandrostane and proceeding as specified in Example 24, 4.2 g. (84%) of the free base are obtained; m.p. 201°–203° C; after recrystallization from a mixture of methanol and water, m.p. 203°–204° C.

The hydrochloride recrystallized from ethanol melts at 226°–228° C.

EXAMPLE 30

3-Oxo-6ξ-piperidino-5β,19-cycloandrostane-17-oxime 2.0 g. (0.005 moles) of 3β-hydroxy-6ξ-piperidino-5β,19-cycloandrostane-17-oxime, 60 ml. of anhydrous toluene and 11 ml. of distilled cyclohexanone are weighed into a round-bottomed 250 ml. flask. In order to remove water from the reaction mixture, 10 ml. of distillate are distilled off, then the distillation is slowly continued, and a solution of 1.06 g. (0.005 moles) of aluminium isopropylate in 10 ml. of anhydrous toluene are dropwise added to the reaction mixture in 30 minutes, meanwhile distilling off 15 ml. of distillate. On continuing the distillation, further 10 ml. of solvent are removed from the system. The residual reaction mixture of jelly-like consistency is transferred into a separating funnel, shaken with 2 × 10 ml. of a saturated aqueous solution of potassium sodium tartrate, then subjected to steam distillation. The residual part is extracted with chloroform, the chloroform phase is washed with water, dried with sodium sulphate and evaporated under vacuum. On rubbing the residue with acetone, 1.50 g. (75%) of crystalline product are obtained; m.p. 197°–200° C; after recrystallization from anhydrous ethanol, m.p. 200°–203° C.

The hydrochloride recrystallized from a mixture of acetone and water melts at 263°–264° C.

EXAMPLE 31

3-Oxo-6ξ-piperidino-17α-ethynyl-17β-hydroxy-5β,19-cycloandrostane 10 g. (0.025 moles) of 3β-hydroxy-6ξ-piperidino-17α-ethynyl-17β-hydroxy-5β,19-cycloandrostane, 54 ml. (0.52 moles) of distilled cyclohexanone and 300 ml. of anhydrous toluene are weighed into a round-bottomed 500 ml. flask equipped with a distilling attachment. 40 ml. of distillate are distilled off under atmospheric pressure, then the distillation is slowly continued, and the solution of 5.1 g. (0.025 moles) of aluminium isopropylate in 40 ml. of anhydrous toluene is dropwise added to the reaction mixture in an hour, meanwhile distilling off about 100 ml. of distillate. After distilling off further 50 ml. of distillate, the residue is cooled to room temperature, shaken with 2 × 20 ml. of a saturated aqueous solution of potassium sodium tartrate, and subjected to steam distillation. The residual part is extracted with 2 × 30 ml. of chloroform. The chloroformic solution is washed with water, dried with sodium sulphate and evaporated under vacuum. The thus-obtained thick, viscous oil is rubbed with some cold acetone. The obtained crystals are washed with acetone and then with petroleum ether (b.p. 30°–40° C), and dried under vacuum at 60° C, affording 6.40 g. (63%) of the product; m.p. 173°–175° C; after recrystallization from a mixture of acetone and water, m.p. 178°–179° C.

EXAMPLE 32

3-Oxo-6ξ-piperidino-17α-ethynyl-17β-acetoxy-5β,19-cycloandrostane 5 g. (0.013 moles) of 3-oxo-6ξ-piperidino-17α-ethynyl-17β-hydroxy-5β,19-cycloandrostane and 5 g. (0.027 moles) of p-toluenesulphonic acid monohydrate are dissolved in 50 ml. of acetic anhydride. The solution is heated to 60° C and kept at this temperature for 1.5 hours, then the reaction mixture is poured onto 300 ml. of ice-water, and allowed to stand for half an hour. The aqueous solution is made alkaline with a 20% solution of sodium hydroxide and extracted with benzene. The benzene phase is washed with water, dried with sodium sulphate and evaporated to dryness under vacuum. The obtained amorphous substance recrystallizes on rubbing with petroleum ether (b.p. 30°–40° C). After filtration, washing with petroleum ether and drying under vacuum at 60° C, 3.80 g. (86%) of the product are obtained; m.p. 142°–145° C.

EXAMPLE 33

6ξ-Piperidino-5β,19-cycloandrostane-3,17-dioxime

A reaction mixture consisting of 5 g. (0.014 moles) of 3,17-dioxo-6ξ-piperidino-5β,19-cycloandrostane, 3.8 g. (0.054 moles) of hydroxylamine hydrochloride, 7.8 g. (0.095 moles) of anhydrous sodium acetate and 130 ml. of anhydrous ethanol is refluxed on a water bath for 2.5 hours. On cooling to room temperature the precipitated salts are filtered off, and the filtrate is evaporated to dryness under vacuum. The residue is dissolved in 100 ml. of water, made alkaline with a 10% solution of sodium carbonate and extracted with benzene. The benzene phase is washed with water, dried with sodium sulphate and evaporated under vacuum. The residue is rubbed with acetone, filtered, washed with acetone and dried under vacuum at 60° C, affording 4.40 g. (81%) of the product; m.p. 222°–223° C.

EXAMPLE 34

3-Oximino-6ξ-piperidino-17α-ethynyl-17β-acetoxy-5β,19-cycloandrostane 3 g. (0.007 moles) of 3-oxo-6ξ-piperidino-17α-ethynyl-17β-acetoxy-5β,19-cycloandrostane and 1.10 g. (0.016 moles) of hydroxylamine hydrochloride are dissolved in 30 ml. of anhydrous pyridine. The solution is warmed for an hour on a boiling water bath. On cooling to room temperature, the reaction mixture is poured onto 200 ml. of ice-water, then made alkaline with a 10% solution of sodium carbonate. The formed precipitate is filtered, washed with water and dried under vacuum over phosphorus pentoxide, affording 2.40 g. (77%) of the product; m.p. 210°–213° C; after recrystallization from a mixture of ethanol and water, m.p. 217°–219° C.

EXAMPLE 35

3β-Acetoxy-6ξ-amino-17-ethylenedioxy-5β,19-cycloandrostane hydrochloride 1.00 g. (1.94 millimoles) of 3β-acetoxy-6ξ-(benzylamino)-17-ethylenedioxy-5β,19-cycloandrostane hydrochloride is dissolved in 20 ml. of water, made alkaline with a 10% solution of sodium hydroxide, and extracted with 3 × 15 ml. of benzene. The benzene phases are combined, washed with water, dried, and evaporated to dryness under vacuum. The residue is dissolved in 25 ml. of ethanol, then hydrogenated at room temperature and under atmospheric pressure in the presence of 0.2 g. of boneblack containing 5% of palladium as catalyst, until the uptake of hydrogen is terminated. On filtering off the catalyst, the filtrate is neutralized by ethanol saturated with hydrochloric acid gas, and the neutral solution is evaporated to dryness under vacuum. The obtained amorphous substance is recrystallized from isopropanol, affording 0.55 g. (66%) of the product; m.p. 189°–192° C.

EXAMPLE 36

3β-Acetoxy-6ξ-[(2'-hydroxyethyl)-amino]-17-ethylenedioxy-5β,19-cycloandrostane hydrochloride 1.00 g. (1.84 millimoles) of 3β-acetoxy-17-ethylenedioxy-19-tosyloxy-Δ⁵-androstene is dissolved by heating in 5 ml. of N,N-dimethyl acetamide and 0.5 ml. (8.40 millimoles) of freshly distilled 2-hydroxyethylamine. The reaction mixture is heated to 110° C and kept at this temperature for 5 hours. After cooling the solution is poured slowly, under continuous stirring, to 50 ml. of a 25% aqueous solution of sodium chloride, and stirred for 15 minutes. The formed precipitate is filtered and dissolved in 30 ml. of benzene. The benzene solution is washed with a saturated aqueous solution of sodium chloride, dried with sodium sulphate and evaporated to dryness under vacuum. The residue is dissolved in 10 ml. of anhydrous ethanol, and neutralized by ethanol saturated with dry hydrochloric acid gas. The neutral solution is evaporated to dryness under vacuum and the residue is rubbed with acetone. The formed crystals are filtered, washed with acetone, and dried under vacuum at 60° C, affording 0.35 g. (40%) of the product; m.p. 199°–202° C; recrystallized from acetone, m.p. 203°–206° C.

What we claim is:

1. A 6-amino-5β,19-cycloandrostane derivative of formula I and its pharmaceutically acceptable acid addition salts

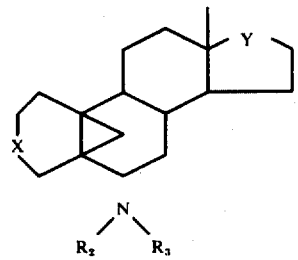

(I)

wherein
X denotes any of the groups of the formula $=CH(OR)$, $=CO$ or $=C=N-OR_1$,
Y denotes any of the groups of the formula $=CO$, $=CH(OR_1)$, $=C=N-OR_1$, $=C(OR_1)-C=CH$ or

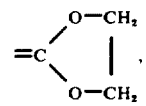

wherein
R denotes a hydrogen atom, a $C_{1-4}$ alkyl group or a $C_{2-5}$ acyl group, and
$R_1$ denotes a hydrogen atom a straight-chained or branched $C_{1-5}$ alkyl group, a straight-chained or branched $C_{1-5}$ hydroxyalkyl group, a $C_{3-8}$ cycloalkyl group, an allyl group, or a benzyl group, and
$R_3$ has the same meaning as $R_2$ but if $R_2$ is a sec. or tert. alkyl group or an alicyclic group, then $R_3$ can only be a hydrogen atom; and if $R_2$ is a benzyl group then $R_3$ can only be a hydrogen atom or a primary alkyl group, further
$R_2$ and $R_3$ may denote together with the adjacent nitrogen atom a piperidine, a morpholine, or an N-methylpiperazine group.

* * * * *